United States Patent
Sato et al.

(10) Patent No.: US 11,278,253 B2
(45) Date of Patent: Mar. 22, 2022

(54) X-RAY DIAGNOSIS APPARATUS AND X-RAY DIAGNOSIS METHOD

(71) Applicant: CANON MEDICAL SYSTEMS CORPORATION, Otawara (JP)

(72) Inventors: Motohiro Sato, Nasushiobara (JP); Hidesuke Tomura, Otawara (JP); Koichi Kaminaga, Shioya (JP); Toshiaki Kondo, Yaita (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 155 days.

(21) Appl. No.: 16/410,165

(22) Filed: May 13, 2019

(65) Prior Publication Data
US 2019/0343479 A1 Nov. 14, 2019

(30) Foreign Application Priority Data
May 14, 2018 (JP) .............................. JP2018-093095

(51) Int. Cl.
*A61B 6/00* (2006.01)
*A61B 6/06* (2006.01)
*A61B 6/08* (2006.01)

(52) U.S. Cl.
CPC ............... *A61B 6/465* (2013.01); *A61B 6/06* (2013.01); *A61B 6/463* (2013.01); *A61B 6/469* (2013.01); *A61B 6/5241* (2013.01); *A61B 6/54* (2013.01); *A61B 6/588* (2013.01); *A61B 6/08* (2013.01); *A61B 6/4021* (2013.01); *A61B 6/488* (2013.01)

(58) Field of Classification Search
CPC .......... A61B 6/463; A61B 6/465; A61B 6/469
See application file for complete search history.

(56) References Cited

U.S. PATENT DOCUMENTS

| 4,649,555 | A | * | 3/1987 | Matsubayashi | A61B 6/469 378/20 |
| 4,856,040 | A | * | 8/1989 | Geluk | A61B 6/032 378/146 |
| 5,682,414 | A | * | 10/1997 | Saito | A61B 6/032 378/146 |
| 2006/0050846 | A1 | * | 3/2006 | Sako | A61B 6/04 378/62 |
| 2016/0361035 | A1 | * | 12/2016 | Lee | A61B 6/545 |
| 2017/0007196 | A1 | * | 1/2017 | Don | A61B 6/4417 |

FOREIGN PATENT DOCUMENTS

| JP | 2004-236910 | 8/2004 |
| JP | 2006-255236 | 9/2006 |
| WO | WO 2015/146526 | 10/2015 |

OTHER PUBLICATIONS

Office Action dated Jan. 25, 2022 in Japanese Office Action 2018-093095.

* cited by examiner

*Primary Examiner* — Chih-Cheng Kao
(74) *Attorney, Agent, or Firm* — Oblon, McClelland, Maier & Neustadt, L.L.P.

(57) ABSTRACT

According to one embodiment, an X-ray diagnostic apparatus includes a display and processing circuitry. The display displays information representing a position of an object corresponding to an irradiation position of an X-ray tube. The processing circuitry receives an operation for adjusting the irradiation position of the X-ray tube based on the information displayed on the display, and controls the X-ray tube based on the irradiation position adjusted by the operation.

14 Claims, 15 Drawing Sheets

X-RAY DIAGNOSIS APPARATUS AND X-RAY DIAGNOSIS METHOD

CROSS-REFERENCE TO RELATED APPLICATIONS

This application claims the benefit of priority of Japanese Patent Application No. 2018-093095, filed May 14, 2018, the entire contents of which are incorporated herein by reference.

FIELD

Embodiments described herein relate generally to an X-ray diagnosis apparatus and an X-ray diagnosis method.

BACKGROUND

An X-ray image generated by an X-ray diagnostic apparatus such as a general radiographic X-ray apparatus or an X-ray TV system is used to observe a position of interest of an object. Less distortion of the X-ray image is desirable in order to make a correct and accurate observation.

However, in the X-ray diagnostic apparatus using an X-ray detector whose detection surface is substantially flat, distortion of an image at a position, among the detection surface, away from the position straight-facing to the center of the focal point of the X-ray tube (hereinafter referred to as the center of the X-ray tube) is larger than that at the position straight-facing to the central position of the X-ray tube. Hence, the X-ray imaging of the position of interest of the object may be preferably performed with the center of the X-ray tube positioned at the straight-facing position of the position of interest of the object.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention. The drawings show.

DETAILED DESCRIPTION

Hereinbelow, a description will be given of an X-ray diagnosis apparatus and an X-ray diagnosis method according to embodiments of the present invention with reference to the drawings. The X-ray diagnostic apparatus according to an embodiment of the present invention is configured to interlock the position of the center of the X-ray tube and the X-ray detector so as to maintain the positional relationship with each other.

In general, according to one embodiment, an X-ray diagnostic apparatus includes a display and processing circuitry. The display displays information representing a position of an object corresponding to an irradiation position of an X-ray tube. The processing circuitry receives an operation for adjusting the irradiation position of the X-ray tube based on the information displayed on the display, and controls the X-ray tube based on the irradiation position adjusted by the operation.

Figure 1:
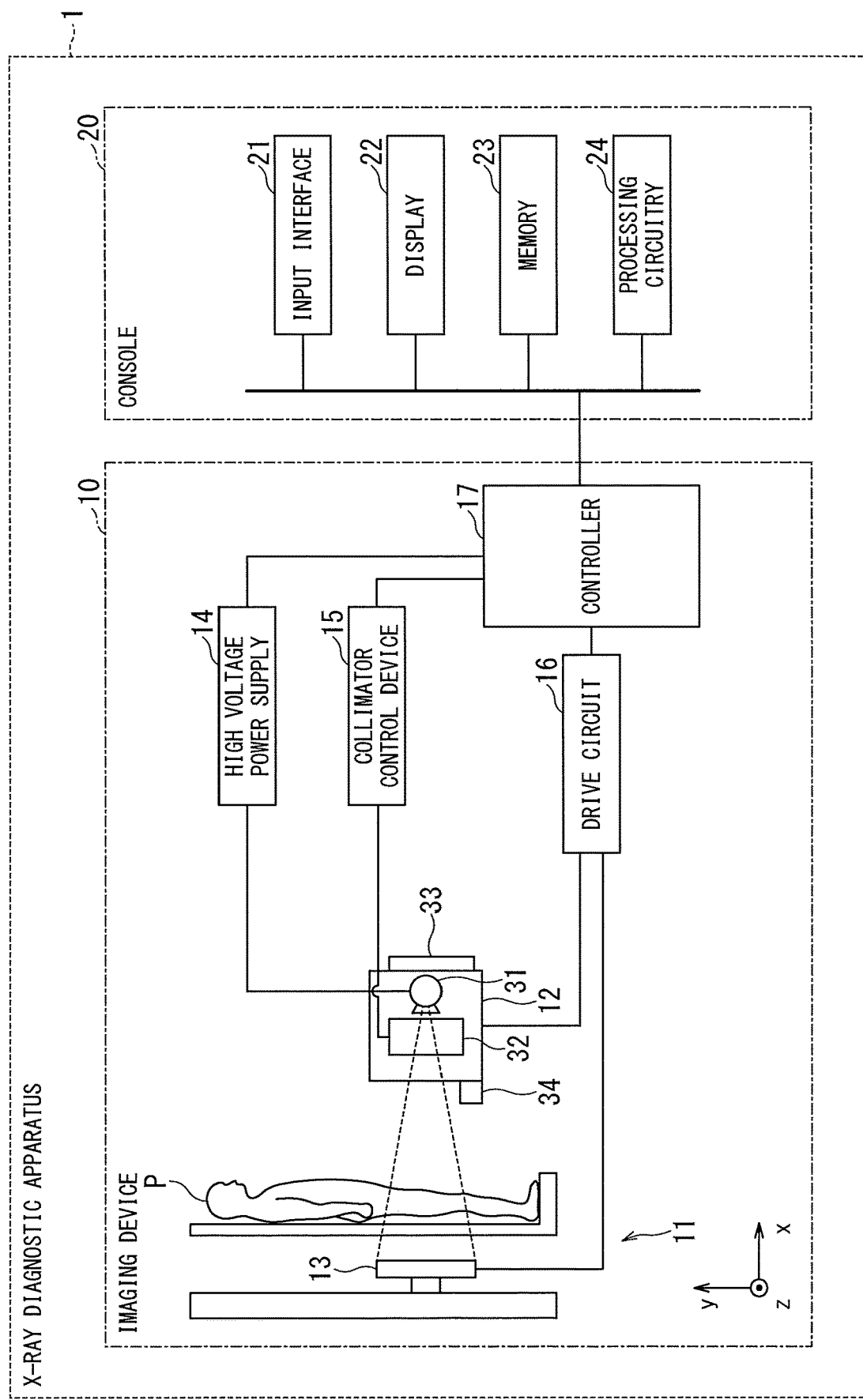
FIG. 1 is a block diagram showing an example of an X-ray diagnostic apparatus according to an embodiment of the present invention.
Figure 2:
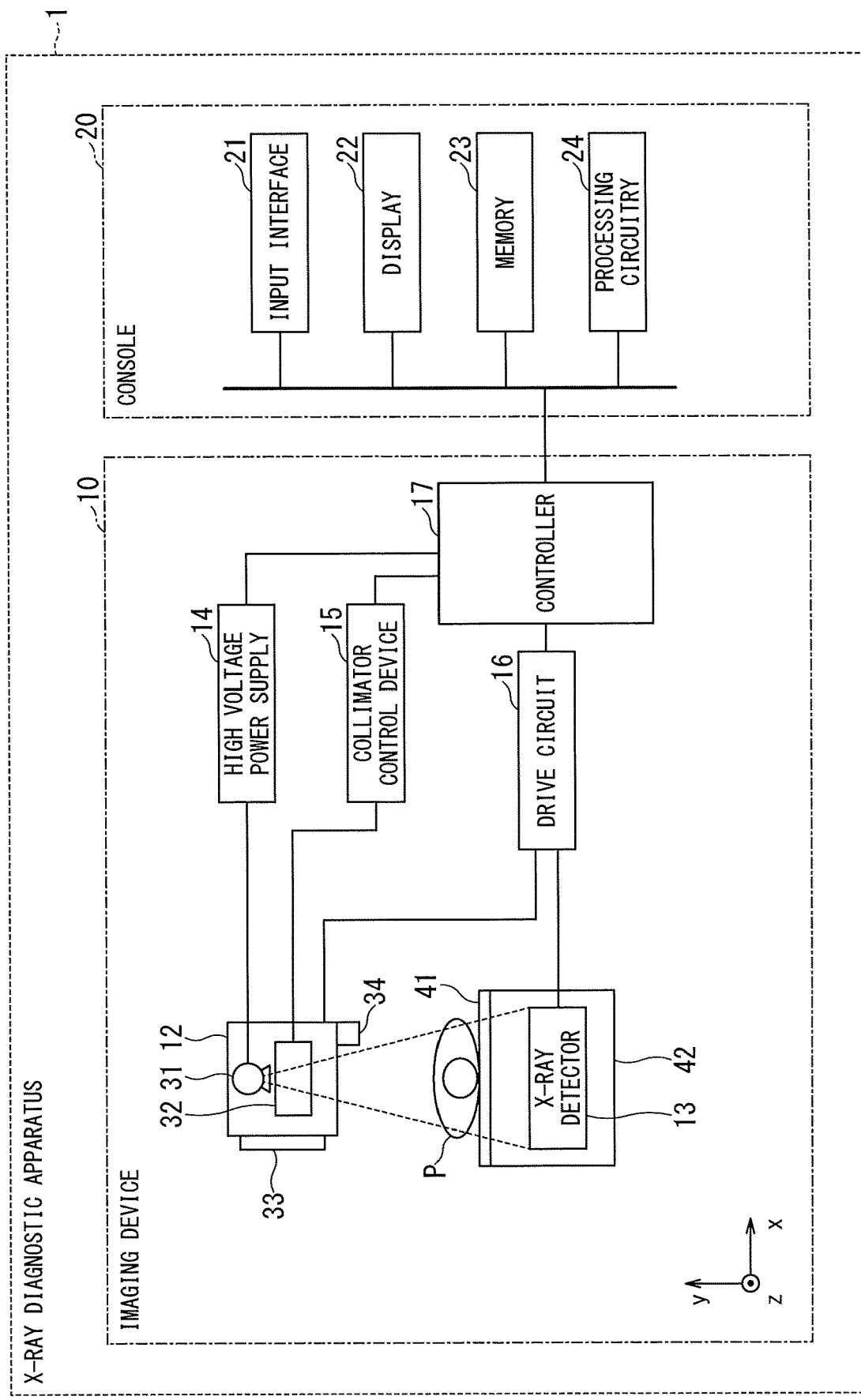
FIG. 2 is a block diagram showing another example of the X-ray diagnostic apparatus.

FIG. 1 is a block diagram showing an example of an X-ray diagnostic apparatus 1 according to an embodiment of the present invention. FIG. 2 is a block diagram showing another example of the X-ray diagnostic apparatus 1. FIG. 1 is an example of X-ray diagnostic apparatus 1 for performing X-ray imaging of the object P in a standing position, and FIG. 2 is an example of X-ray diagnostic apparatus 1 for performing X-ray imaging of the object P in a decubitus position.

The X-ray diagnostic apparatus 1 includes an imaging device 10 and a console 20 as shown in FIGS. 1 and 2.

The imaging device 10 includes a stand 11, an X-ray tube holding device 12, an X-ray detector 13 movably supported with respect to the stand 11, a high voltage power supply 14, a collimator control device 15, a drive circuit 16, and a controller 17. When performing X-ray imaging of the object P in a decubitus position, as shown in FIG. 2, the imaging device 10 has a bed 42 provided with a top plate 41 on which the object P is placed instead of the stand 11.

The X-ray tube holding device 12 of the imaging device 10 has an X-ray tube 31, a collimator 32, an operation panel 33, and a camera 34.

When performing X-ray imaging of the object P in the standing position, as shown in FIG. 1, the object P stands in front of the stand 11. The X-ray tube holding device 12 and the X-ray detector 13 are controlled by the controller 17 via the drive circuit 16, and can be interlocked to maintain the positional relationship between the central position of the X-ray tube 31 and the position of the X-ray detector 13. For example, the X-ray detector 13 supported by the stand 11 moves along the stand 11 in conjunction with the movement of the X-ray tube holding device 12 such that the central position of the X-ray tube 31 and the position of the approximate center of X-ray detector 13 face with each other.

When performing X-ray imaging of the object P in the decubitus position is X-ray imaged, the object P in the decubitus position is placed on the top plate 41 as shown in FIG. 2. In this case, as in the case of the standing position, the X-ray tube holding device 12 and the X-ray detector 13 are controlled by the controller 17 via the drive circuit 16, and can be interlocked to maintain the positional relationship between the central position of the X-ray tube 31 and the position of the X-ray detector 13.

The X-ray detector 13 is constituted by a flat panel detector (FPD) having a plurality of X-ray detection elements arranged in a two-dimensional array, detects an X-ray irradiated to the X-ray detector 13 through the object P, and outputs projection data of the X-ray based on this detected X-ray. This projection data is given to the console 20 through the controller 17. The X-ray detector 13 may include an image intensifier, a TV camera and the like.

The X-ray tube 31 is a vacuum tube which irradiates thermoelectrons from the cathode (filament) to the anode (target) by applying a high voltage from the high voltage power supply 14. The X-ray tube 31 is disposed opposite to the X-ray detector 13 across the object P. The X-ray tube 31 is controlled by the controller 17 via the drive circuit 16 and is moved in conjunction with the movement of X-ray detector 13 such that the central position of the X-ray tube 31 and the approximate central position of the X-ray detector 13 remains opposite to each other.

The high voltage power supply 14 is composed of an electric circuit such as a transformer and a rectifier, and includes a high voltage generator having a function of generating a high voltage to be applied to the X-ray tube 31 and an X-ray control device that controls the output voltage according to the X-ray emitted by X-ray tube 31.

The collimator 32 has a plurality of blades made of metal that blocks X-rays such as lead. The collimator 32 has a mechanism for adjusting the X-ray radiation field generated by the X-ray tube 31. The collimator 32 is controlled by the controller 17 via the collimator control device 15 to adjust the irradiation range of the X-ray irradiated from the X-ray tube 31.

The operation panel 33 is provided on the body of the X-ray tube holding device 12 and has a hard key, such as a button for outputting a unique instruction signal to the processor when pressed by the user, and a display input device. The display input device includes a display as a display unit and a touch sensor as an input unit provided in the vicinity of the display.

The display of the operation panel 33 displays various images such as an image showing information regarding the X-ray diagnostic apparatus 1 and a reference image of the object P taken by the camera 34. The user can input various instructions for the image displayed on the display to the X-ray diagnostic apparatus 1 via the touch sensor or hard key of the operation panel 33. The operation panel 33 provides the processing circuitry of the console 20 with a signal according to the user input.

The camera 34 is provided to the body of the X-ray tube holding device 12. The camera 34 is configured by a charge coupled device (CCD) type image sensor or a complementary metal oxide semiconductor (CMOS) type image sensor, and captures the image of the object P in the standing position on the stand 11 or the object P in the decubitus position on the top plate 41, and provides the captured image to the processing circuitry 24 of the console 20 via controller 17. The camera 34 may be attached with a wide-angle lens or a fisheye lens so as to obtain a wider range of the camera image of the object P. The camera 34 may be provided on a wall, including the ceiling, of the examination room. The X-ray diagnostic apparatus 1 may not have the camera 34.

The controller 17 at least includes a processor and a memory. The controller 17 is controlled by the console 20 in accordance with the program stored in the memory to generally control components of the imaging device 10. For example, by controlling the X-ray irradiation system, the controller 17 performs long-size imaging for generating a long-size image of the object P, generates projection data, and provides it to the console 20.

Meanwhile, the console 20 has an input interface 21, a display 22, a memory 23, and a processing circuitry 24. The console 20 may not be provided independently. For example, the operation panel 33 of the imaging device 10 may have the functions of the input interface 21 and the display 22 of the console 20, and the functions of the memory 23 and the processor and the memory of the controller 17 may have the functions of the processing circuitry 24 and the memory 23, respectively.

The input interface 21 of the console 20 includes, for example, a general pointing device such as a joystick, a trackball, a trackball mouse, a keyboard, a touch panel, a ten key, a hand switch for instructing X-ray emission timing, and provides operation signals corresponding to the user operation to the processing circuitry 24.

The display 22 is configured by a general display output device such as a liquid crystal display or an OLED (Organic Light Emitting Diode) display, and displays information in accordance with the control of the processing circuitry 24.

The memory 23 has a configuration including a processor readable recording medium such as a magnetic or optical recording medium or a semiconductor memory, and some or all of the programs and data in the storage medium may be configured to be downloaded via an electronic network.

The processing circuitry 24 is a processor configured to execute a procedure to adjust the irradiation position of the X-ray tube 31 based on the position of the object P corresponding to the irradiation position of the X-ray tube 31 and to perform X-ray imaging, by reading out and executing the program stored in the memory 23. Further, the processing circuitry 24 controls the entire operation of the imaging device 10 via the controller 17.

Here, the distortion of the X-ray image affected by the positional relationship between the center of the X-ray tube 31 (the focal point of the X-ray tube 31) and the position of interest will be described. In the following description, the X-ray image includes a long-size image.

The X-ray detector 13 of the X-ray diagnostic apparatus 1 is composed of an FPD having a plurality of X-ray detection elements arranged in two dimensions, an image intensifier, a TV camera, for example, and the X-ray detection plane is arranged in flat. Therefore, X-rays emitted from the X-ray tube 31 to the object P and detected by the X-ray detector 13 diverge, conically or collimated into a square pyramid, from the focal point of the X-ray tube 31, and are directed to the X-ray detector 13.

Hence, among the positions of the X-ray detector 13, the X-ray is incident at almost zero incident angle on the detection surface of the X-ray detector 13 at the straight faced position to the center of the X-ray tube 31, while X-rays are incident on the detection surface at some incident angle at a position away from the straight faced position to the center of the X-ray tube 31. The distortion of the image therefore becomes greater at a position away from the straight faced position to the center of the X-ray tube 31 than at the position straight faced to the center of the X-ray tube 31. When the position of interest deviates from the position straight faced to the center of the X-ray tube 31, the observation of the position of interest using the X-ray image is adversely affected by this fact. This problem also arises in the distance measurement between two points of interest using a long-size image.

Figure 3:
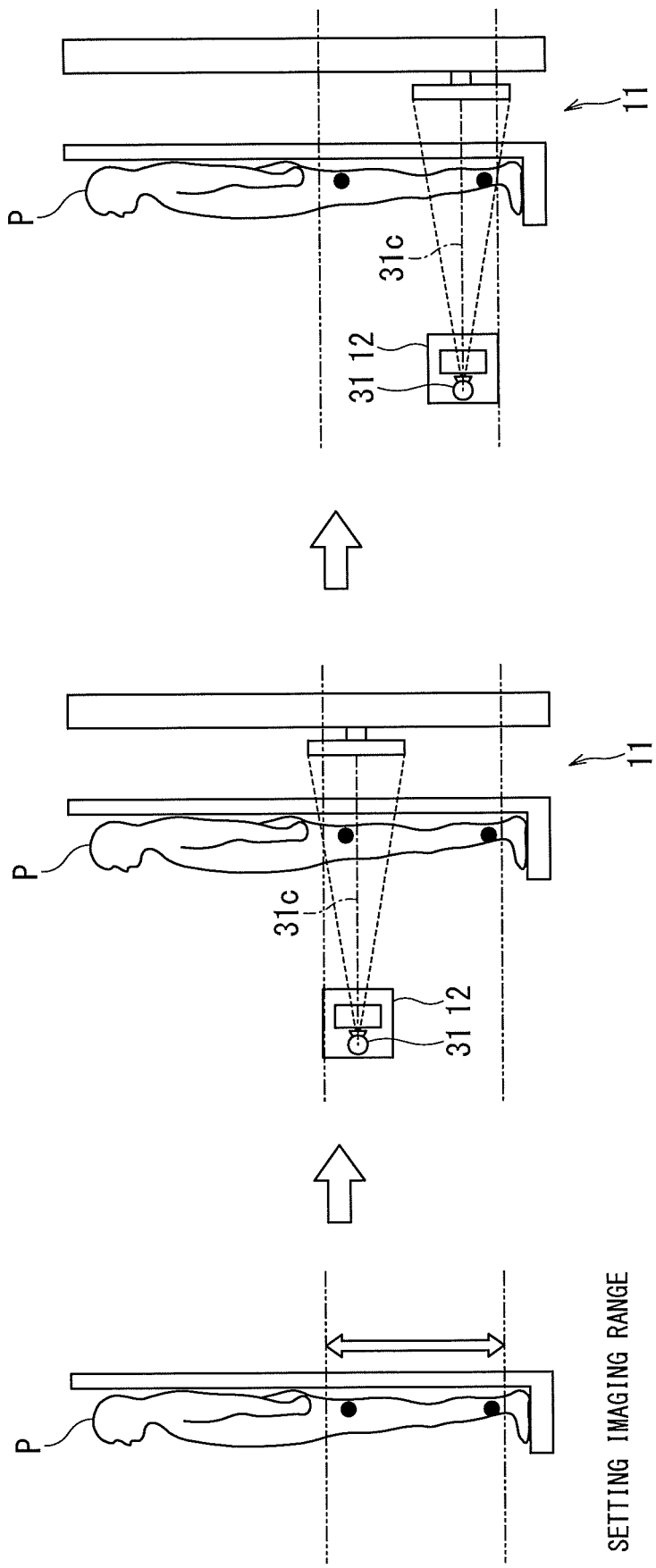
FIG. 3 is an explanatory diagram showing an example of a conventional long-size imaging procedure for generating a conventional long-size image.

FIG. 3 is an explanatory diagram showing an example of a conventional long-size imaging procedure for generating a conventional long-size image.

When measuring the distance between two positions of interest (see two black circles in FIG. 3) on the long-size image, the longitudinal imaging range in the long-size image is set to include the two interest positions (see left of FIG. 3). Then, in accordance with the set imaging range, a plurality of imaging regions constituting the imaging range are automatically set so as to partially overlap with each other in the longitudinal direction. FIG. 3 shows an example of the case where the imaging range is configured by two upper and lower imaging regions.

However, in the prior art, the relationship between the position of the center of the X-ray tube 31 and the position of interest is not considered in each X-ray imaging of each imaging region when the imaging region is automatically set. In the example shown in FIG. 3, the position 31c of the center of the X-ray tube 31 in the X-ray imaging of the upper imaging region is set to be positioned considerably lower than the upper interest position (See middle image of FIG. 3). Further, the position 31c of the center of the X-ray tube 31 in the X-ray imaging of the lower imaging region is set to be positioned severely above the lower interest position (see right image of FIG. 3).

As shown in FIG. 3, the position of the center of the X-ray tube 31 may be largely deviated from the straight faced position corresponding to the position of interest at each X-ray imaging of each imaging region for generating a long-size image in the conventional method. In this case, the image at the position of interest in the long-size image is to be an image with distortion. Therefore, it is very difficult to accurately measure the distance between two points of interest with this long-size image.

To cope with this problem, the X-ray diagnostic apparatus 1 according to the present embodiment displays information representing the position of the object P corresponding to the irradiation position of the X-ray tube 31 (hereinafter referred to as irradiation position information), and receives the operation for adjusting the irradiation position of the X-ray tube 31 by the user referring to the irradiation position information, whereby the irradiation position of the X-ray tube 31 can be positioned at a desired position of the user when X-ray imaging is performed.

Figure 4:
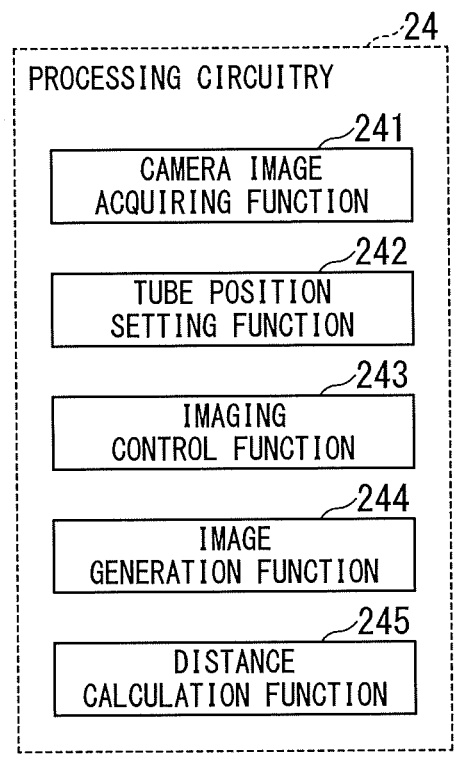
FIG. 4 is a schematic block diagram showing an example of functions of processor of the processing circuitry.

FIG. 4 is a schematic block diagram showing an example of functions of processor of the processing circuitry 24. The processor of the processing circuitry 24 implements a camera image acquiring function 241, a tube position setting function 242, an imaging control function 243, an image generation function 244, and a distance calculation function 245 as shown in FIG. 4. Each of these functions is stored in memory 23 in the form of a program.

In this embodiment, an example in which each function 241-245 is realized by the processing circuitry 24 of the console 20 will be described. However, some or all of the functions 241-245 of the processing circuitry 24 may be realized by the controller 17, or realized by an external device independent of the X-ray diagnostic apparatus 1 such as an in-hospital server, a cloud console, a workstation or the like connected to the network, which has at least a processor and a storage circuit.

When the X-ray diagnostic apparatus 1 includes the camera 34, the camera image acquiring function 241 acquires a wide angle camera image of the object P captured by the camera 34 as a reference image. When the X-ray diagnostic apparatus 1 does not include the camera 34, the processing circuitry 24 may not realize the camera image acquiring function 241.

Figure 5A:
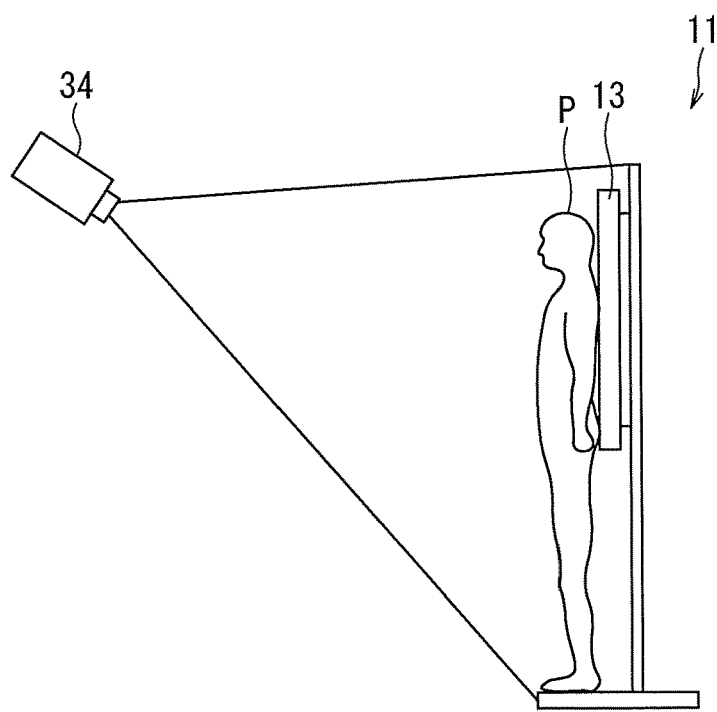
FIG. 5A is an explanatory diagram showing an example of capturing camera image by a camera of the X-ray diagnostic apparatus shown in FIG. 1.
Figure 5B:
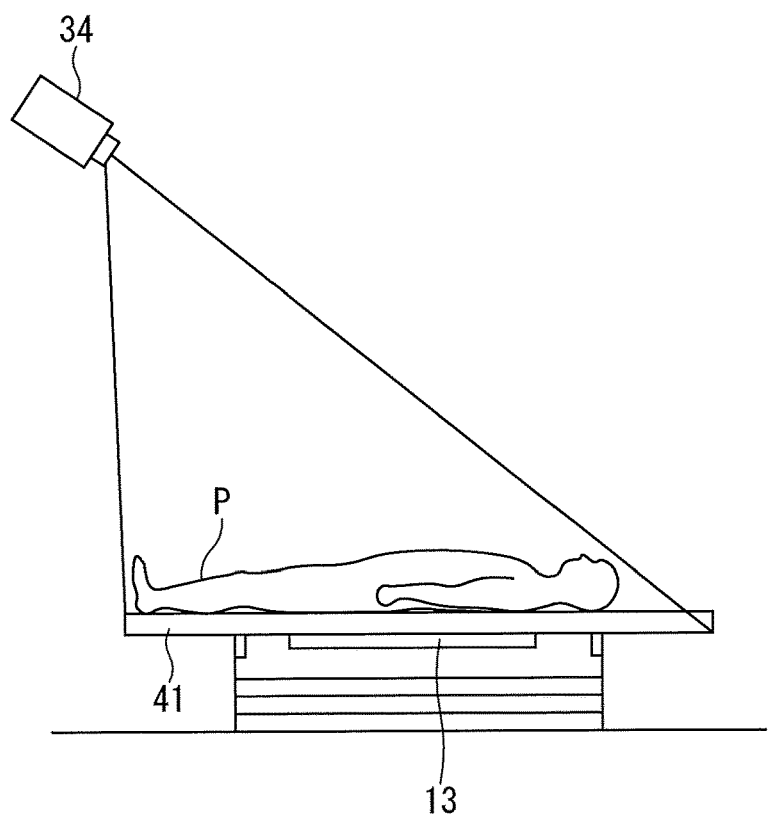
FIG. 5B is an explanatory diagram showing an example of capturing camera image by a camera of the X-ray diagnostic apparatus shown in FIG. 2.

FIG. 5A is an explanatory diagram showing an example of capturing camera image by the camera 34 of the X-ray diagnostic apparatus 1 shown in FIG. 1. FIG. 5B is an explanatory diagram showing an example of capturing camera image by the camera 34 of the X-ray diagnostic apparatus 1 shown in FIG. 2.

As shown in FIG. 5A, the camera 34 of the X-ray tube holding device 12 captures the object P standing in front of the stand 11 to generate the camera image, and provides it to the camera image acquiring function 241. As shown in FIG. 5B, the camera 34 of the X-ray tube holding device 12 captures the object P at the decubitus position placed on the top 41 to generate the camera image, and provides it to the camera image acquiring function 241. The camera 34 may capture the object P so as to include at least all the positions of interest. FIG. 5 shows an example in which the camera 34 is provided with a wide-angle lens, and the camera 34 captures the object P so as to include the entire body of the object P.

The tube position setting function 242 displays the information representing the position of object P corresponding to the irradiation position of the X-ray tube 31 (irradiation position information) on the operation panel 33 of the X-ray tube holding device 12 and/or the display 22 of the console 20. The irradiation position information may be information indicating the positional relationship between the irradiation position and the position of the object P. The irradiation position information includes coordinate information of the irradiation position, the name of the site of the object P corresponding to the irradiation position, and an image in which an image such as a marker indicating the irradiation position and a reference image such as a camera image of the object P are superimposed. The irradiation position indicated by the marker may be the position of the center of X-ray tube 31 or a position surrounding the position of the center of X-ray tube 31 (for example, the position of the vertex of the polygon surrounding the position of the center, the position of the center and the like).

For example, when the X-ray diagnostic apparatus 1 includes the camera 34 and the reference image of the object P based on the camera image captured by the camera 34 is available, the tube position setting function 242 displays the reference image of the object P on the operation panel 33 of the X-ray tube holding device 12 and/or the display 22 of console 20.

As the reference image of object P, a human body atlas may be used instead of the camera image. When physical information of the object P such as the height of object P can be obtained from the examination order, it is preferable to use a human body atlas corresponding to the physical size of object P.

Further, the tube position setting function 242 receives a user operation for adjusting the irradiation position of the X-ray tube 31 based on the displayed irradiation position information, and sets the irradiation position. The user operation is received based on, for example, a touch operation on the operation panel 33 and an input operation via the input interface 21. The user operation for adjusting the irradiation position of the X-ray tube 31 includes an operation of specifying the irradiation position by coordinates and an operation of specifying a name of a site of the object P.

Figure 6A:
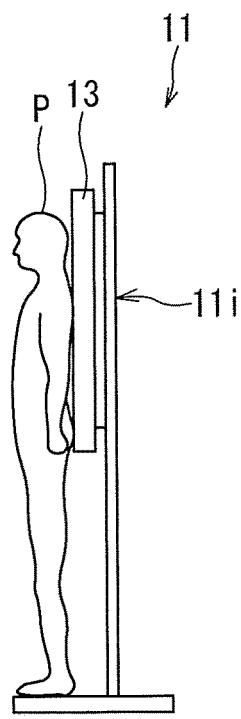
FIG. 6A illustrates a side view showing an example of a stand input interface of the X-ray diagnostic apparatus shown in FIG. 5A.
Figure 6B:
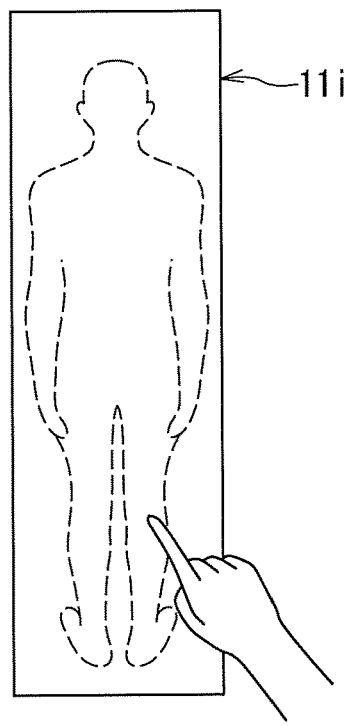
FIG. 6B illustrates a rear view showing an example of the stand input interface.

FIG. 6A illustrates a side view showing an example of a stand input interface 11i of the X-ray diagnostic apparatus 1 shown in FIG. 5A. FIG. 6B illustrates a rear view showing an example of the stand input interface 11i.

As shown in FIGS. 6A and 6B, a stand input interface 11i for receiving user input may be integrally provided, or may be detachably attached, on the back of the stand 11. In this case, the user can adjust the irradiation position of the X-ray tube 31 via the stand input interface 11i based on the displayed irradiation position information (information representing the position of the object P corresponding to the irradiation position of the X-ray tube 31).

As shown in FIG. 6B, the stand input interface 11i may be a touch sensor that constitutes a touch panel having a length equal to or larger than the height of the object P. When the stand input interface 11i is a touch sensor constituting a touch panel, the tube position setting function 242 may display the irradiation position information on the display of the touch panel. Alternately or additionally, the stand input interface 11i may be configured of a plurality of designated switches, and the irradiation position of the X-ray tube 31 may be determined according to the pressed designated switch. In this case, the plurality of designation switches may be provided with a distribution density that allows the user to designate the position of interest without a large positional error, regardless of the height of the object P. Further, the stand input interface 11i is configured by, for example, motion switches for moving the irradiation position in the upper, lower, left, and right directions, and the irradiation position may be determined according to the time durations or the number of times the upper, lower, left, and right motion switches are pressed. Further, the stand input interface 11i may be configured to be able to specify the name of the site of the object P.

A configuration corresponding to the stand input interface 11i may be provided in the X-ray diagnostic apparatus 1 (see FIG. 2) that performs X-ray imaging of the object P in the decubitus position. In this case an input interface may be provided on the side surface of the top plate 41 or the bed 42. The input interface is configured of a touch sensor, designation switches, or motion switches as well, and the user may adjust the irradiation position via the input interface.

An example will be described in the following description in which the X-ray diagnostic apparatus 1 includes camera 34, and the tube position setting function 242 sets the center position of the X-ray tube 31 (Hereinafter, the set center position is referred to as the set position) at the time of X-ray imaging of object P based on the input to the reference image. When performing long-size imaging, the tube position setting function 242 determines the set position for each of imaging regions constituting the imaging range of the long-size image based on the user input in the reference image.

At this time, the user gives an input operation such that a position corresponding to the position of interest included in the reference image or a position corresponding to the vicinity thereof is set as the position (set position) of the center of the X-ray tube 31, in order to reduce distortion of the image at the position of interest in the X-ray image. In this case, the user may click with a mouse or touch the position of interest included in the reference image or the vicinity thereof. The tube position setting function 242 sets the position corresponding to the position of the object P on the reference image designated by the user, that is, the straight faced position of the designated position, as the set position of the center of the X-ray tube 31.

When the user desires to measure the distance between two interest positions, the user may input an instruction to set the position corresponding to the position of interest or the vicinity thereof as the set position of the center of the X-ray tube 31 for each of at least two interest positions included in the reference image.

The tube position setting function 242 may display the irradiation position image such as a reference image on the display of the operation panel 33 provided on the X-ray tube holding device 12, or on the display 22 of the console 20, or on both of them. When the irradiation position image is displayed on the display of the operation panel 33, the user can confirm the reference image without leaving the imaging device 10, and can perform input on the reference image via the touch panel of the operation panel 33 on the spot.

The coordinates of the reference image displayed on the display of the operation panel 33 and the coordinates of the X-ray tube 31 in the real space may be associated in advance.

The imaging control function 243 controls the X-ray tube 31, the X-ray detector 13, and the collimator 32 such that the center of X-ray tube 31 is moved to the set position and X-ray imaging of object P is performed at that position. When long-size imaging is performed, the imaging control function 243 moves the center of the X-ray tube 31 to the set position and performs X-ray imaging, for each of a plurality of imaging regions constituting the imaging range of the long-size image.

The image generation function 244 generates an X-ray image based on the X-ray imaging and causes the display of the operation panel 33 to display the X-ray image. For example, in the case of long-size imaging, the image generation function 244 generates a long-size image based on the X-ray imaging performed on each of a plurality of imaging regions, and causes the display of the operation panel 33 to display the long-size image.

The distance calculation function 245 receives operations on the X-ray image for specifying points on the X-ray image, each point being corresponding to each of at least two set positions, and calculates the distance between two specified points in terms of the body length conversion value.

Figure 7:
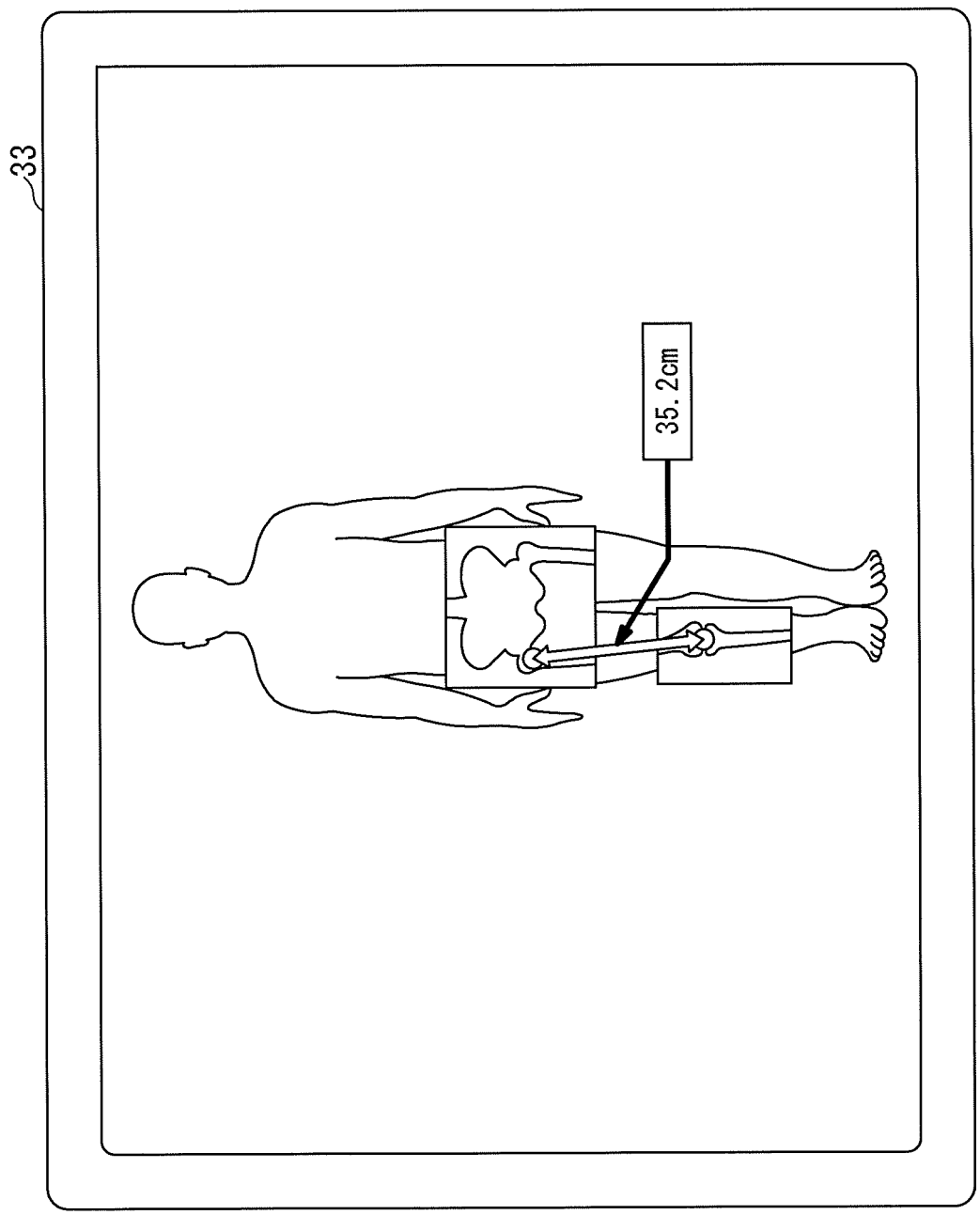
FIG. 7 is an explanatory diagram showing an example of distance calculation by a distance calculation function according to the embodiment.

FIG. 7 is an explanatory diagram showing an example of distance calculation by the distance calculation function 245 according to the embodiment. FIG. 7 shows an example in which the set position of the center of the X-ray tube 31 is set in two places. In this case, the X-ray imaging is performed twice at each of the two set positions. The image generation function 244 causes the display of the operation panel 33 to display the X-ray images superimposed on the reference image, where each of the X-ray images is corresponding to each of the two X-ray imagings.

For each of the two set positions, the user specifies the position on the X-ray image corresponding to the set position or the vicinity thereof, via the operation panel 33. Then, the distance calculation function 245 calculates the distance between the two specified points.

The position on the X-ray image corresponding to the set position of the center of the X-ray tube 31 is the position set by the user by specifying at or vicinity of the position of interest on the reference image. The image at or vicinity of the position in the X-ray image corresponding to the set position of the X-ray tube 31 is an image generated based on the X-rays incident on the X-ray detector 13 perpendicularly from the center of the X-ray tube 31, and hence an image with less distortion. Thus, the distance calculation function 245 can calculate the distance between two points accurately.

Various methods are conventionally known as methods of calculating the distance between two points specified on the X-ray image, and the distance calculation function 245 may use any of these methods. For example, when the X-ray detector 13 is configured by the two-dimensionally arranged X-ray detection element, the distance between the two points can be calculated based on the positions of the X-ray detection element in the X-ray detector 13 corresponding to the specified 2 pixels and the movement distance of the X-ray detector 13 between two X-ray imagings correspond to the two specified points.

Since the X-ray detector 13 moves in conjunction with the X-ray tube 31, the moving distance of the X-ray detector 13 matches the moving distance of the X-ray tube 31. Therefore, when the X-ray detection elements corresponding to two specified points are located at the center of X-ray detector 13, for example, the distance between the two points is equal to the movement distance of X-ray detector 13, i.e., the movement distance of the X-ray tube 31.

Further, Although FIG. 7 shows an example in which two points are designated when two X-ray images corresponding to two X-ray imagings are separated, two points may be designated on a long-size image generated by partially overlapping a plurality of X-ray images. Even when two points are specified on the long-size image, if the position of each of the two designated points is a position on the X-ray image corresponding to the set position of the X-ray tube 31 or a position vicinity of that position, the distance calculation function 245 can calculate the distance between two points accurately.

Next, a method of setting the central position of the X-ray tube 31 for each imaging region in the case of generating a long-size image will be described.

Figure 8:
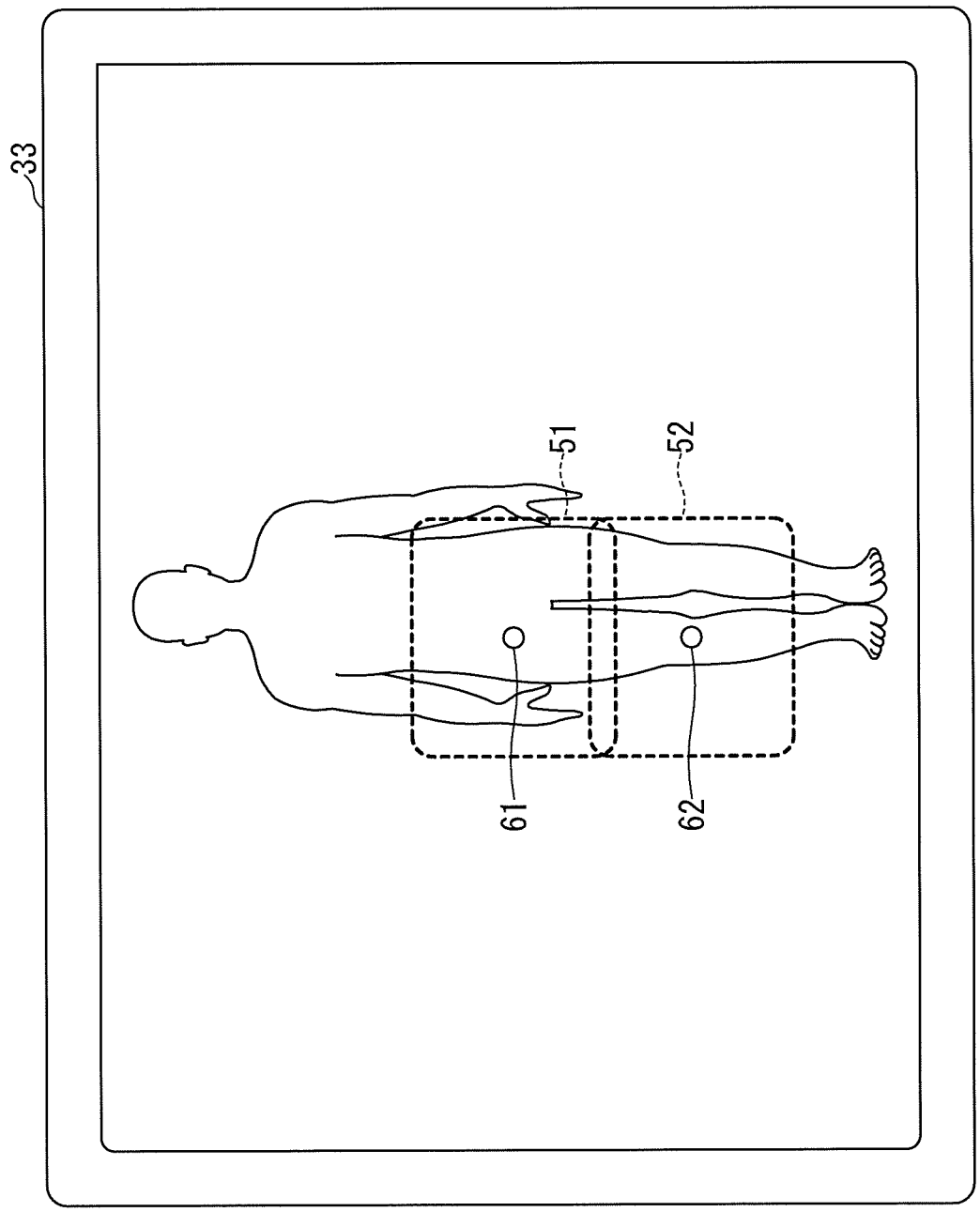
FIG. 8 is an explanatory diagram showing an example of an displayed initial image of setting receiving image of central position of X-ray tube for long-size imaging.

FIG. 8 is an explanatory diagram showing an example of a displayed initial image of setting receiving image of central position of X-ray tube 31 for long-size imaging.

When performing the long-size imaging, the tube position setting function 242 sets the imaging range in the longitudinal direction (longitudinal ends) of the long-size image. Then, according to the size of the imaging range, a plurality of imaging regions are set automatically so as to partially overlap each other in the longitudinal direction. FIG. 8 shows an example in which two regions, an upper region 51 and a lower region 52, are set as imaging regions constituting the imaging range of the long-size image and are superimposed on the reference image depicting the whole body of object P.

As a method of setting the imaging range, a method of setting based on an imaging protocol, or a method of manually specifying by the user, may be used. As a method of manually specifying by the user may be a method in which a light indicating a virtual irradiation range of X-rays is projected toward the object P from an emitter such as a laser pointer (not shown) provided on the X-ray tube holding device 12, the user moves the X-ray tube holding device 12 with confirming this projected light, and the user enters, at the top and bottom of the desired imaging range, an instruction to set each position as the top and bottom via the operation panel 33.

When setting multiple imaging regions constituting the imaging range of a long-size image, if the overlapping region of the initially set imaging regions is located at the avoidance area, the overlapping region may be moved to a position avoiding the avoidance area by the user input or automatically by processing circuitry 24. This kind of avoidance area includes, for example, sensitive portions such as the eyeballs and the genitals of object P. Since the portion located in the overlapping region is exposed to the exposure twice, it is not preferable that the sensitive portion is located in the overlapping region.

Furthermore, the user may designate the avoidance area as the irradiation prohibited area via the operation panel 33, the input interface 21, the stand input unit 11i, and the like. When the irradiation prohibited area is designated, the imaging control function 243 controls the collimator 32 such that the X-rays are not irradiated to the irradiation prohibited area.

The tube position setting function 242 may superimpose an image (Hereafter referred to as setting position corresponding image) indicating the initial position of the position corresponding to the set position of the center of the X-ray tube 31 on the reference image of the object P, for each imaging region. The image in which the setting position corresponding image is superimposed on the reference image of the object P is an example of the irradiation position information (information indicating the position of the object P corresponding to the irradiation position of the X-ray tube 31). The initial position may be the center of each imaging region. FIG. 8 shows an example in which the initial positions of the setting position corresponding images 61 and 62 are set at the centers of the upper region 51 and the lower region 52, respectively, and superimposed on the reference image of the object P.

The initial position of the imaging region and the initial position of the setting position corresponding image may be determined based on the imaging region and the set position in the X-ray imaging performed in the past. In this case, the tube position setting function 242 acquires the information of the imaging region in the X-ray imaging performed in the past and the information of the set position of the center of the X-ray tube 31 from the memory 23 or from the database via the network. Then, the tube position setting function 242 may superimpose the position of the imaging region in the past and the set position in the past on the reference image and cause the display of the operation panel 33 display the images as initial positions of the current imaging region and the current set position.

Figure 9:
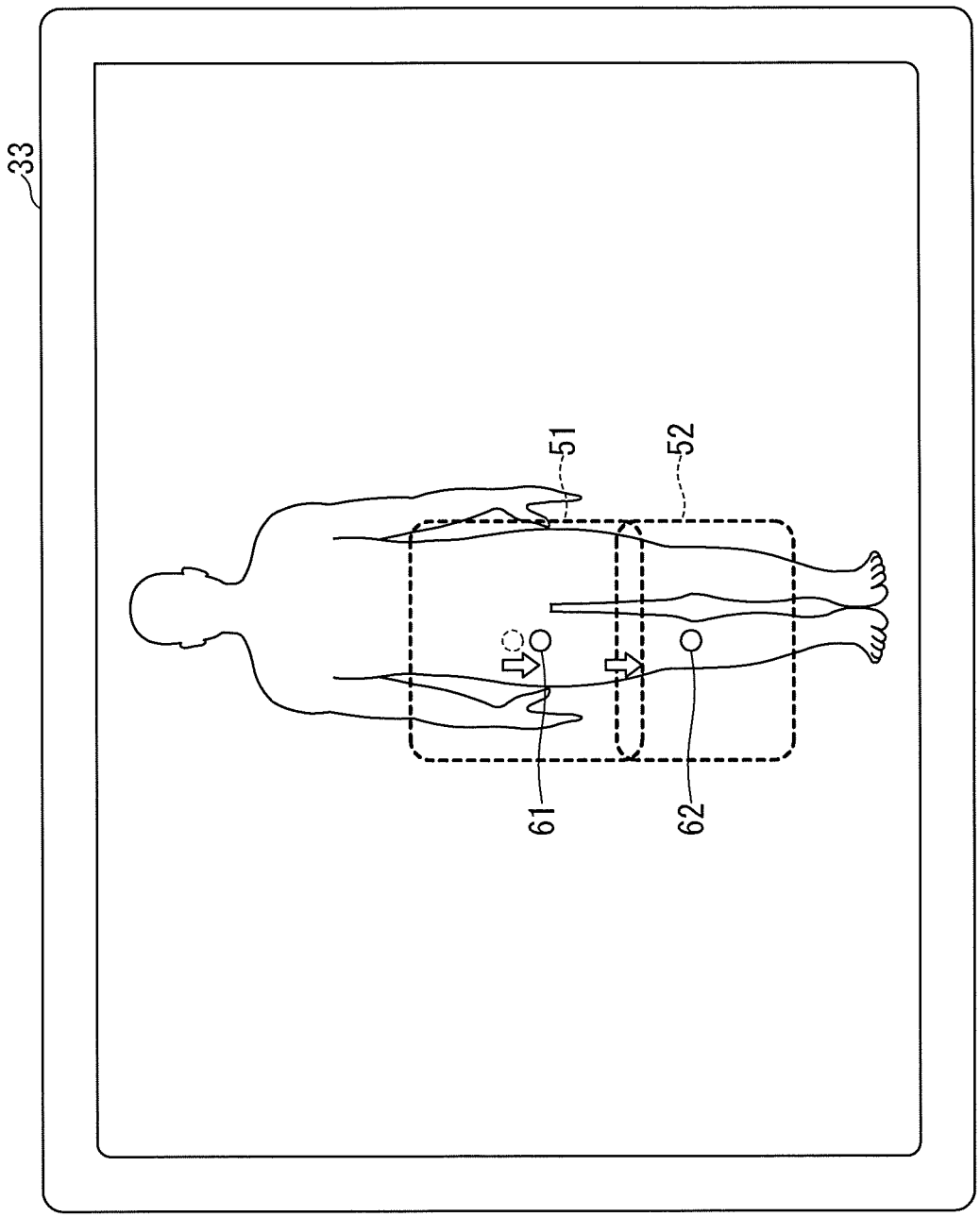
FIG. 9 is an explanatory diagram showing an example in the case where a set position corresponding image is adjusted in the longitudinal direction of the imaging range with respect to the initial image shown in FIG. 8.

FIG. 9 is an explanatory diagram showing an example in the case where a setting position corresponding image 61 is adjusted in the longitudinal direction of the imaging range with respect to the initial image shown in FIG. 8.

Now, suppose that the user desires to measure the distance from the base of the right leg to the right knee. In this case, the base of the right leg and the right knee are the positions of interest, and the X-ray image of each position of interest is desired to be X-ray imaged with the center of the X-ray tube 31 positioned straight facing to each position of interest. However, in the initial image shown in FIG. 8, although the initial position of the setting position corresponding image 62 in the lower region 52 is located at or near the position of the right knee, the initial position of the setting position corresponding image 61 in the upper region 51 is deviated greatly from the position of interest.

Therefore, as shown in FIG. 9, the user may give an input instruction via the operation panel 33 such that the setting position corresponding image 61 of the upper region 51 is located at or vicinity of the desired position of interest. The tube position setting function 242 determines the position straight facing to the position of the user-specified setting position corresponding image 61 as the set position of the center of the X-ray tube 31. The imaging control function 243 moves the center of the X-ray tube 31 to this set position, and controls the X-ray tube 31, the X-ray detector 13, and the collimator 32 to perform X-ray imaging of object P at that position. Then, the image generation function 244 generates a long-size image based on the X-ray imaging performed on each of the plurality of imaging regions, and causes the display of the operation panel 33 to display the long-size image.

As a result, the image at the position of interest in the long-size image generated by the image generation function 244 has less distortion. Therefore, the distance calculation function 245 can accurately calculate the distance between the positions of interest.

When the setting position corresponding image 61 gets too close to the overlapping region of the imaging regions, the tube position setting function 242 may reset each of the imaging regions such that the distance along the longitudinal direction between the overlapping region and the set position is equal to or more than a threshold (see FIG. 9). Image processing such as blending is performed on a superimposed region where different X-ray images are combined and pasted. However, when image processing is performed, there is a risk that the X-ray image may be blurred. For this reason, when the distance along the longitudinal direction between the overlapping region and the set position is smaller than the threshold, it is preferable to reset each of the imaging regions such that blending processing is not performed on the position of interest. In the example shown in FIG. 9, the imaging control function 243 controls the collimator 32 via the collimator control device 15 such that the changed upper region 51 is irradiated with X-rays according to the changed upper region 51 and the central position of the X-ray tube 31.

The reset of the imaging region to move the overlapping region may be performed automatically by the tube position setting function 242, or may be performed semi-automatically in response to an operation such as the user directly dragging the overlapping region displayed on the operation panel 33. When resetting the imaging region semi-automatically, the system enters the movement mode of the overlapping region when the user long-presses the overlapping region, and the tube position setting function 242 receives an operation for moving the overlapping region by the subsequent drag operation, and then the tube position setting function 242 may reset the imaging region in response to this drag operation. Further, regardless of automatic or semi-automatic, resetting of the imaging region to move the overlapping region may be performed in order to prevent overlapping of the position of interest and the overlapping region, or may be performed in order to prevent the overlapping of the above-mentioned avoidance area and the overlapping region.

While making it possible to flexibly move the overlapping region as mentioned above, it is preferable to make the positions of both ends in the longitudinal direction of the imaging range unchanged from the viewpoint of exposure.

Figure 10:
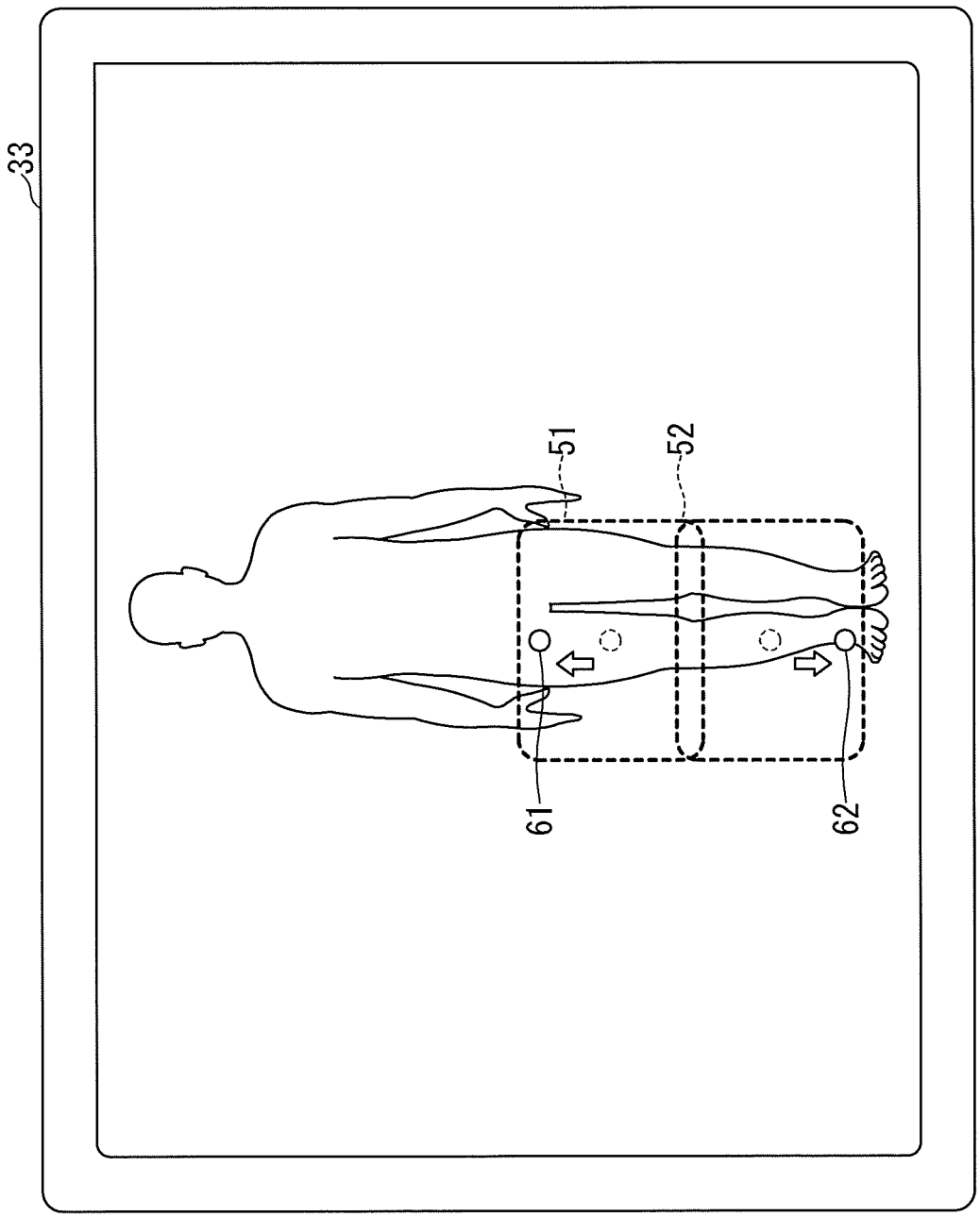
FIG. 10 is an explanatory diagram showing an example in which a set position corresponding image is adjusted in the longitudinal direction of the imaging range while keeping both end positions of the imaging range in the longitudinal direction unchanged with respect to the initial image shown in FIG. 8.

FIG. 10 is an explanatory diagram showing an example in which a setting position corresponding image 61 is adjusted in the longitudinal direction of the imaging range while keeping both end positions of the imaging range in the longitudinal direction unchanged with respect to the initial image shown in FIG. 8. FIG. 10 shows an example in which the setting position corresponding image 61 of the upper region 51 is specified to be located at the base of the right leg and the setting position corresponding image 62 of the lower region 52 is specified to be located at the right ankle. As shown in FIG. 10, in consideration of the dose of object P, the positions of both ends may be kept unchanged even when the setting position corresponding image 61 approaches both longitudinal ends of the imaging range. Further, in consideration of the hardware movement limit of the collimator 32, the settable position of the setting position corresponding image 61 may be a position separated by a predetermined distance in the longitudinal direction from both ends of the imaging range. In this case, in addition to the images 51 and 52 indicating the imaging region, an image indicating the settable limit of the setting position corresponding image 61 may be superimposed and displayed.

Figure 11:
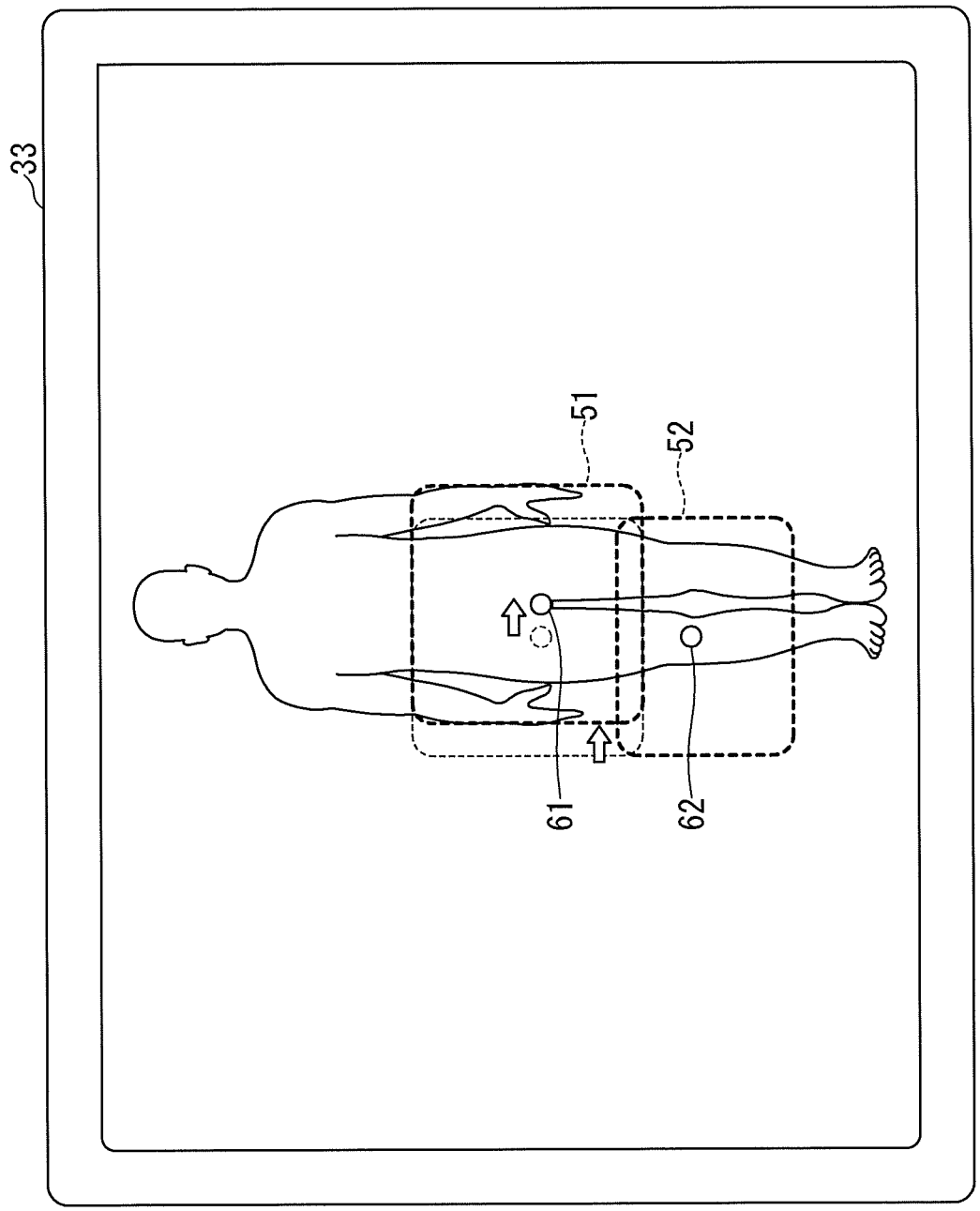
FIG. 11 is an explanatory diagram showing an example in the case where a set position corresponding image is adjusted in a short-length direction of the imaging range.

FIG. 11 is an explanatory diagram showing an example in the case where a setting position corresponding image 61 is adjusted in a short-length direction of the imaging range. FIG. 11 shows an example where the setting position corresponding image 61, after adjustment in the longitudinal direction as shown in FIG. 9, is further adjusted to the short-length direction. As shown in FIG. 11, the user can also move the setting position corresponding image in the short-length direction of the imaging range. Also in this case, as shown in FIGS. 9 and 10, the tube position setting function 242 determines the position straight facing to the position of the setting position corresponding image 61 on the reference image as the set position of the center of the X-ray tube 31. The imaging control function 243 moves the center of X-ray tube 31 to this set position, and controls the X-ray tube 31, the X-ray detector 13, and the collimator 32 to perform X-ray imaging of object P at that position.

The case where the setting position corresponding image is superimposed on the reference image of object P and displayed for each imaging region when generating the long-size image has been described with reference to FIGS. 8-11. However, the setting position corresponding image may not be displayed regardless of whether or not the long-size image is generated. Even when the setting position corresponding image is not displayed, the user may directly specify the set position via the operation panel 33 such that the set position of the center of X-ray tube 31 is located straight facing to the desired position of interest or its vicinity.

When generating the long-size image, the user may indicate in advance the number of imaging regions that constitute the imaging range of the long-size image. In this case, the tube position setting function 242 superimposes imaging regions of this preset number on the reference image. The setting position corresponding image may not be displayed, and the set position may be set based on the direct designation by the user on the reference image for each imaging region, i.e., the instruction not for adjusting the setting position corresponding image but for directly specifying the central position.

Figure 12:
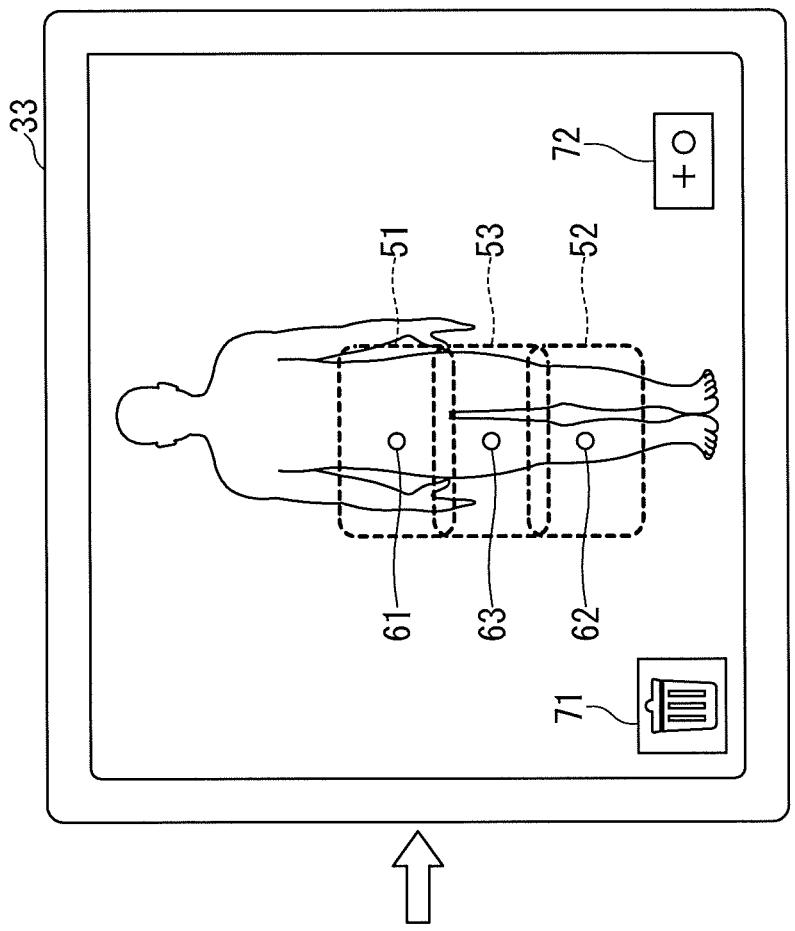
FIG. 12 is an explanatory diagram showing an example of a change receiving image for changing the number of imaging regions constituting the imaging range of the long-size image.
Figure 12:
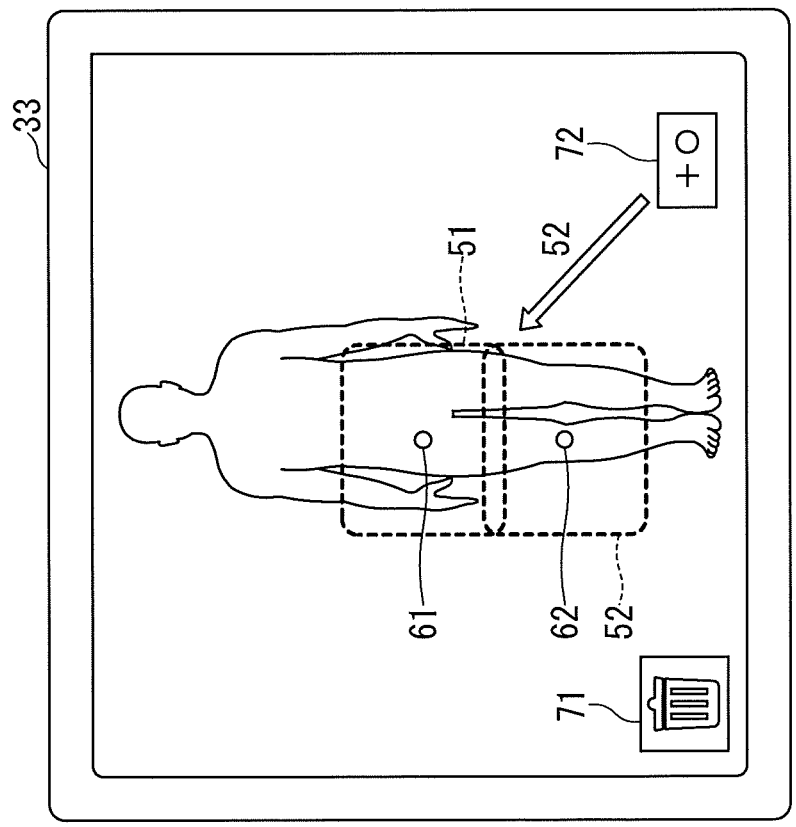

FIG. 12 is an explanatory diagram showing an example of a change receiving image for changing the number of imaging regions constituting the imaging range of the long-size image.

As shown in FIG. 12, the change receiving image for changing the number of imaging regions may include a trash can icon 71 for reducing the number of imaging regions and an addition icon 72 for adding the number of imaging regions. In the example shown in FIG. 8, it is assumed that the user desires to add a third imaging region 53 between the upper region 51 and the lower region 52. In this case, the user can add a third imaging region 53 at a desired position in the change receiving image displayed on the display of the operation panel 33 by dragging the add icon 72 to the position between the upper area 51 and the lower area 52.

In this assumption, the tube position setting function 242 resets the positions of all the added imaging regions and the positions of the setting position corresponding images according to the added imaging regions. Further, the tube position setting function 242 may display the setting position corresponding image 63 at the center of the imaging region 53 as an initial position (see FIG. 12). The user can easily delete any imaging region by dragging the imaging region considered unnecessary to the trash can icon 71. Also in this case, the tube position setting function 242 resets the positions of all imaging regions and the positions of the setting position corresponding images after deletion.

Next, an example of the operation of the X-ray diagnostic apparatus and the X-ray diagnostic method according to the present embodiment will be described.

Figure 13:
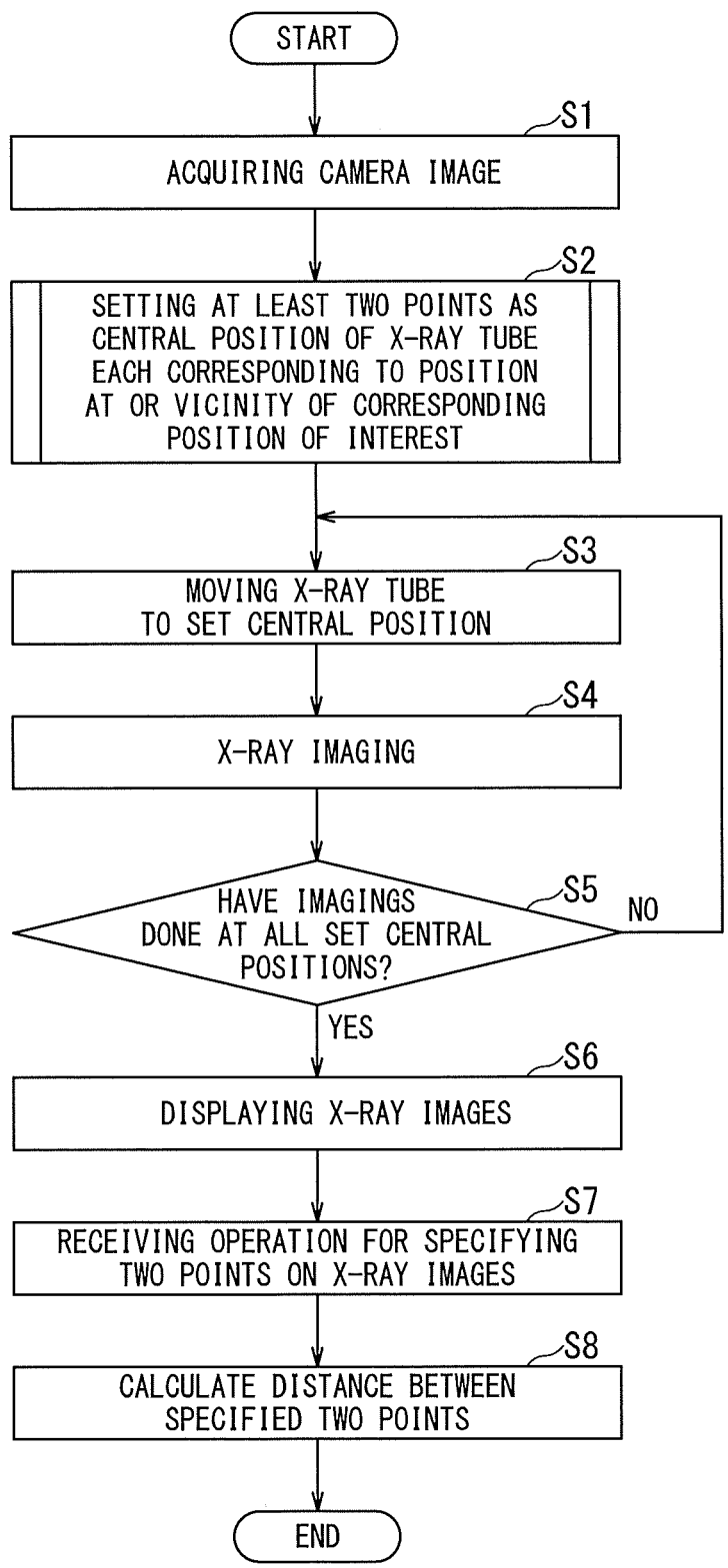
FIG. 13 is a flowchart showing an example of a procedure implemented by the processing circuitry of the X-ray diagnostic apparatus shown in FIG. 1 for performing X-ray imaging with easily locating the center of the X-ray tube straight facing to the position of interest, for correctly calculating the distance between the positions of interests specified on the X-ray image.

FIG. 13 is a flowchart showing an example of a procedure implemented by the processing circuitry 24 of the X-ray diagnostic apparatus 1 shown in FIG. 1 for performing X-ray imaging with easily locating the center of the X-ray tube 31 straight facing to the position of interest, for correctly calculating the distance between the positions of interests specified on the X-ray image. A reference character with "S" followed by a number in FIG. 13 denotes each step of the flowchart. FIG. 13 shows an example of the procedure in the case where the camera image can be used as a reference image and the user desires to measure the distance between two interest positions.

First, in step S1, the camera image acquiring function 241 acquires a camera image obtained by capturing the object P as a reference image from the camera 34.

Next, in step S2, for each of at least two positions of interest included in the reference image, the user inputs an instruction for specifying each position of interest or vicinity thereof to set the central position of X-ray tube 31. Then, the tube position setting function 242 sets the set position of the center of the X-ray tube 31 such that each position straight faces to the corresponding position of interest specified by the user or vicinity thereof.

Next, in step S3, the imaging control function 243 moves the center of the X-ray tube 31 to the set positions of the center of the X-ray tube 31, i.e., to each of the straight facing positions of at least two interest positions or in the vicinity thereof.

Next, in step S4, the imaging control function 243 controls the X-ray tube 31, the X-ray detector 13, and the collimator 32 to perform X-ray imaging of the object P.

Next, in step S5, the imaging control function 243 determines whether or not X-ray imaging has been done at all set positions. When there is a set position that has not been X-ray imaged yet, then the procedure returns to step S3. On the other hand, when X-ray imaging is performed at all set positions, the image generation function 244 generates an X-ray image based on the X-ray imaging in step S6, and causes the display of the operation panel 33 to display the X-ray image.

Next, in step S7, the user specifies the position on the X-ray image corresponding to the set position or the position in the vicinity thereof using the operation panel 33 for each of the two set positions. The distance calculation function 245 receives information on the positions of the two designated points.

Then, in step S8, the distance calculation function 245 calculates the distance between the two designated points (see FIG. 7).

According to the above procedure, X-ray imaging can be performed with easily positioning the center of the X-ray tube 31 straight facing to the position of interest, and the distance between the positions of interest specified on the X-ray image can be correctly calculated.

Figure 14:
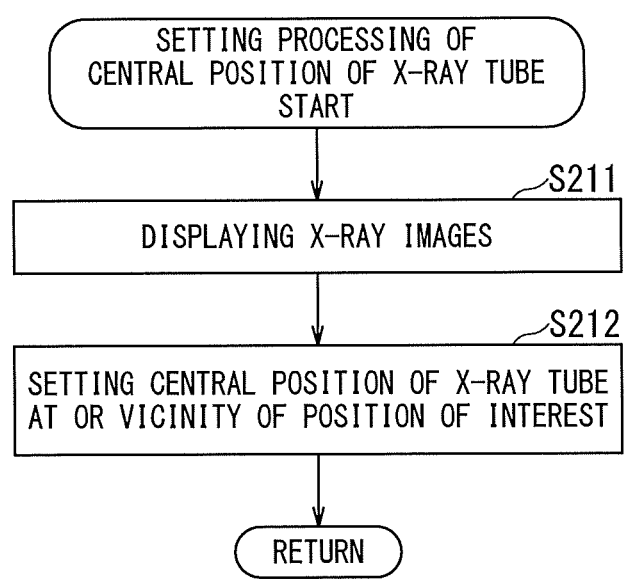
FIG. 14 is a subroutine flowchart showing an example of a procedure for setting processing of the central position of the X-ray tube by a tube position setting function implemented in Step S2 of FIG. 13.

FIG. 14 is a subroutine flowchart showing an example of a procedure for setting processing of the central position of the tube by a tube position setting function 242 implemented in Step S2 of FIG. 13. FIG. 14 is an example of a procedure in the case where multiple X-ray images are separated from one another (see FIG. 7).

In step S211, the tube position setting function 242 causes the display of the operation panel 33 to display the camera image of the object P as the reference image.

Next, in step S212, the tube position setting function 242 sets the set position of the center of the X-ray tube 31 such that each position straight faces to the corresponding position of interest specified by the user or vicinity thereof, and the procedure proceeds to step S3 of FIG. 13. When the tube position setting function 242 displays an image indicating the initial position of the set position of the center of the X-ray tube 31 superimposed on the reference image (see the set position corresponding images 61 and 62 in FIG. 8), then the user may adjust the position of the image showing this initial positions. Meanwhile, when the image indicating the initial position of the set position is not displayed, then the user may directly specify the set position via the operation panel 33.

According to the above procedure, even when a plurality of X-ray images are separated from each other, the user can easily set the center of the X-ray tube 31 for the X-ray imaging of each X-ray image at the position straight facing to the position of interest or the vicinity thereof.

Figure 15:
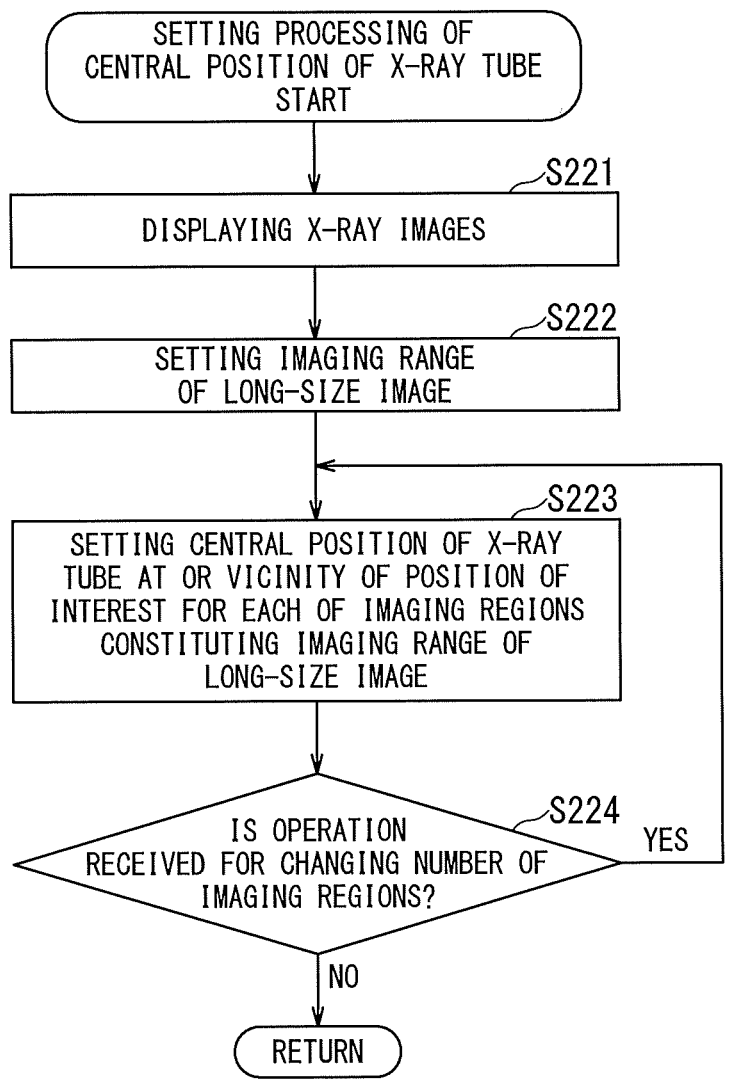
FIG. 15 is a subroutine flowchart showing another example of a procedure for setting processing of the central position of the X-ray tube by the tube position setting function implemented in Step S2 of FIG. 13.

FIG. 15 is a subroutine flowchart showing an another example of a procedure for setting processing of the central position of the tube by the tube position setting function 242 implemented in Step S2 of FIG. 13. FIG. 15 is an example of a procedure in the case of generating a long-size image (see FIGS. 8-12).

In step S221, the tube position setting function 242 causes the display of the operation panel 33 to display the camera image of the object P as the reference image.

Next, in step S222, the tube position setting function 242 sets the imaging range in the longitudinal direction (both ends in the longitudinal direction) of the long-size image based on the user input or based on the imaging protocol. The user may determine the number of imaging regions that constitute the imaging range of the long-size image.

Next, in step S223, based on the user input on the reference image, the tube position setting function 242 sets the position straight facing to the interest position included in the reference image or the vicinity thereof as the center position of the X-ray tube 31.

When images showing the imaging regions according to the imaging range (see the upper region 51 and the lower region 52 in FIG. 8) and images showing the initial positions of the set position of the center of X-ray tube 31 (the setting position corresponding image 61 and 62 in FIG. 8) are superimposed on the reference image and displayed by the tube position setting function 242, the user can adjust the set position by changing the position of the image showing the set position of the center of X-ray tube 31 on the reference image (see FIGS. 9-11).

Further, the tube position setting function 242 may display only images indicating the imaging region according to the imaging range superimposed on the reference image (see the upper region 51 and the lower region 52 in FIG. 8). In this case, the user may directly specify the set position via the operation panel 33 such that the set position of the center of X-ray tube 31 is located straight facing to the desired position of interest or its vicinity.

Furthermore, when the user determines the number of imaging regions in step S222, the tube position setting function 242 superimposes imaging regions of this preset number on the reference image. In this case, the tube position setting function 242 may set the set position based on the direct designation of the central position by the user on the reference image for each imaging region.

Next, in step S224, the tube position setting function 242 determines whether an operation for changing the number of imaging regions has been received. When there is the operation for changing the number of imaging regions (see FIG. 12), the procedure returns to step S223. On the other hand, when there is no operation for changing the number of imaging regions, the procedure proceeds to step S3 in FIG. 13.

According to the above procedure, even when generating a long-size image, the user can easily set the set position of the center of the X-ray tube 31 at the position straight facing to the position of interest or the vicinity thereof for the X-ray imaging of each of a plurality of imaging regions constituting the imaging range of the long-size image.

The X-ray diagnostic apparatus 1 according to the present embodiment displays the irradiation position information (information indicating the position of the object P corresponding to the irradiation position of the X-ray tube 31), and receives the operation for adjusting the irradiation position of the X-ray tube 31 by the user referring to the irradiation position information, whereby the irradiation position of the X-ray tube 31 can be positioned at a desired position when the X-ray imaging is performed. Thus, the X-ray diagnostic apparatus 1 displays the reference image of object P, and set the position of the center of X-ray tube 31 based on the user input of the center position of the X-ray tube 31 on the reference image. Therefore, the user can easily and reliably position the center of the X-ray tube 31 at the position straight facing to the position of interest or the vicinity thereof for the X-ray imaging, thereby the image of the position of interest in the X-ray image being an image with less distortion. Since the X-ray image has less distortion, the user can observe the position of interest very accurately. Further, for each of the two positions of interest, since the X-ray imaging can be performed with positioning the center of the X-ray tube 31 straight facing to the position of interest or vicinity thereof, the distance between the two positions of interest can be accurately measured based on the images with less distortion.

When the X-ray diagnostic apparatus 1 is for performing X-ray imaging of the object P in the standing position as shown in FIGS. 1, 5A, and 6A, the object P can be X-ray imaged in the standing position, i.e., with gravity applied to the joints of the object P. When measuring the distance between two interest positions of the object P in order to fabricate an orthosis such as a lower limb brace, the X-ray imaging of the object P in the standing position is better than in the decubitus position, because the X-ray imaging of the object P in the standing position can make more reasonable measurements in line with the real life of object P.

According to at least one of the above-described embodiments, the irradiation position of the X-ray tube 31 can be adjusted to perform the X-ray imaging based on the position of the object P corresponding to the irradiation position of the X-ray tube 31.

The processing circuitry in the above-described embodiments is an example of the processing circuitry described in the claims. In addition, the term "processor" used in the explanation in the above-described embodiments, for instance, refer to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing corresponding program. When a plurality of processors are provided for the processing circuitry, the memory medium for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
    an X-ray tube;
    an X-ray detector having a flat X-ray detection surface, a position of the X-ray detector being controlled such that a positional relationship between a central position of the X-ray tube and the position of the X-ray detector is maintained;
    a display configured to display information representing a position of an object corresponding to an irradiation position of the X-ray tube for each imaging region of a plurality of imaging regions, the irradiation position of the X-ray tube being the central position of the X-ray tube; and
    processing circuitry configured to
        receive an operation for adjusting each central position of the X-ray tube within the each of the plurality of imaging regions based on the information displayed on the display, and
        control the X-ray tube based on the each central position adjusted for the each of the plurality of imaging regions by the operation.

2. The X-ray diagnostic apparatus according to claim 1, wherein the processing circuitry is configured to
    receive an operation for specifying a position of interest of the object as the operation for adjusting the central position of the X-ray tube, and
    control the X-ray tube based on the position of interest of the object specified by the operation.

3. The X-ray diagnostic apparatus according to claim 1, wherein
    the information representing the position of the object corresponding to the irradiation position of the X-ray tube is an image superimposed on a reference image of the object, and
    the processing circuitry is configured to receive an operation on the reference image for adjusting the central position of the X-ray tube.

4. The X-ray diagnostic apparatus according to claim 1, wherein:
    the display displays the plurality of imaging regions that constitutes an imaging range in a longitudinal direction of a long-size image of the object and is superimposed on a reference image; and
    the processing circuitry is configured to:
        receive the operation for adjusting each of the central positions of the X-ray tube within each of the plurality of imaging regions,
        control the X-ray tube based on the each central position of the X-ray tube adjusted for the each of the plurality of imaging regions, and
        generate the long-size image based on X-rays irradiated by the X-ray tube in each of the plurality of imaging regions.

5. The X-ray diagnostic apparatus according to claim 4, further comprising a collimator adjusting an irradiation range of X-rays irradiated from the X-ray tube,
    wherein the processing circuitry is configured to
        change a central position of the X-ray tube corresponding to at least one of the plurality of imaging regions from an initial position based on the operation on the reference image, while making unchanged positions of both ends of the imaging range in the longitudinal direction, and
        control the collimator based on the plurality of imaging regions adjusted by the operation and based on the changed central position of the X-ray tube.

6. The X-ray diagnostic apparatus according to claim 5, wherein the processing circuitry is configured to
    change the central position of the X-ray tube corresponding to the at least one of the plurality of imaging regions from the initial position based on the operation on the reference image, and set the each of the plurality of imaging regions in accordance with a change in the central position of the X-ray tube such that a distance between a region where the plurality of imaging regions overlap with each other and the central position of the X-ray tube is equal to or greater than a threshold value, and
    control the collimator based on the set plurality of imaging regions.

7. The X-ray diagnostic apparatus according to claim 4, wherein the processing circuitry is configured to
    set in advance a number of the plurality of imaging regions that constitute the imaging range of the long-size image based on user input,
    cause the display to display the set number of the plurality of imaging regions superimposed on the reference image, and
    set, for each of the set number of the plurality of imaging regions, the central position of the X-ray tube based on the operation on the reference image.

8. The X-ray diagnostic apparatus according to claim 4, wherein the processing circuitry is configured to
    change a number of the plurality of imaging regions that is superimposed on the reference image and displayed, based on user input and,
    set the central position of the X-ray tube for each of the plurality of imaging regions of the changed number.

9. The X-ray diagnostic apparatus according to claim 4, wherein the processing circuitry is configured to change, in a short-length direction of the long-size image, the central position of the X-ray tube corresponding to at least one of the plurality of imaging regions from an initial position based on the operation on the reference image.

10. The X-ray diagnostic apparatus according to claim 1, wherein the processing circuitry is configured to
    acquire information of a past set position that is a central position of the X-ray tube in X-ray imaging performed in the past,
    cause the display to display the past set position, superimposed on a reference image, as an initial position of the central position of the X-ray tube, and
    set the central position of the X-ray tube for a current X-ray imaging based on an operation to the past set position.

11. The X-ray diagnostic apparatus according to claim 1, further comprising a camera configured to capture a reference image of the object, wherein
    the camera is provided to a body holding the X-ray tube.

12. The X-ray diagnostic apparatus according to claim 1, wherein the processing circuitry is configured to
    receive an operation on an X-ray image for specifying two points, each of the two points on the X-ray image corresponding to the position at or vicinity of each of at least two adjusted central positions by the operation, and
    calculate a distance between the specified two points.

13. The X-ray diagnostic apparatus according to claim 1, wherein the processing circuitry is configured to receive an operation for specifying an irradiation prohibited area in the object, and control a collimator adjusting an irradiation range of X-rays irradiated from the X-ray tube so as to avoid the irradiation prohibited area.

14. An X-ray diagnostic method of controlling an X-ray diagnostic apparatus including an X-ray tube and an X-ray detector that has a flat X-ray detection surface, a position of the X-ray detector being controlled such that a positional relationship between a central position of the X-ray tube and the position of the X-ray detector is maintained, the X-ray diagnostic method comprising:

displaying information representing a position of an object corresponding to an irradiation position of the X-ray tube for each imaging region of a plurality of imaging regions, the irradiation position of the X-ray tube being the central position of the X-ray tube;

receiving an operation for adjusting each central position of the X-ray tube within the each of the plurality of imaging regions based on the information displayed on the display; and controlling the X-ray tube based on the each central position adjusted for the each of the plurality of imaging regions by the operation.

* * * * *